United States Patent

Engelhardt et al.

[11] Patent Number: 5,840,321
[45] Date of Patent: Nov. 24, 1998

[54] HYDROPHILIC, HIGHLY SWELLABLE HYDROGELS

[75] Inventors: Fritz Engelhardt, Frankfurt am Main; Uwe Stüven, Bad Soden, both of Germany; Thomas Daniel, Chesapeake, Va.; Norbert Herfert, Altenstadt, Germany

[73] Assignee: Clariant GmbH, Frankfurt, Germany

[21] Appl. No.: 676,590

[22] Filed: Jul. 8, 1996

[30] Foreign Application Priority Data

Jul. 7, 1995 [DE] Germany ............... 195 24 724.8

[51] Int. Cl.$^6$ ............... A61K 31/78; A61K 31/765
[52] U.S. Cl. ............... 424/402; 524/275; 524/277; 424/484; 424/486; 424/487
[58] Field of Search ............... 264/309, 72; 524/275, 524/277; 424/402, 484, 486, 487

[56] References Cited

FOREIGN PATENT DOCUMENTS

| | | |
|---|---|---|
| 096 790 | 5/1983 | European Pat. Off. . |
| 612 533 | 1/1994 | European Pat. Off. . |
| 29 10 374 | 9/1990 | Germany . |
| 44 14 117 | 10/1995 | Germany . |
| 128709 | 8/1982 | Japan . |
| 94/22940 | 10/1994 | WIPO . |

OTHER PUBLICATIONS

Database WPI, Section Ch, Week 8237, Derwent Publications Ltd., London GB; Class A14, AN 82–7814OE.

*Primary Examiner*—Thurman K. Page
*Assistant Examiner*—P. Kulkosky
*Attorney, Agent, or Firm*—Connolly and Hutz

[57] ABSTRACT

The present invention relates to hydrophilic, highly swellable hydrogels which are coated with nonreactive, water-insoluble waxes in a quantity of from about 0.05 to about 2% by weight, based on uncoated hydrogel.

16 Claims, No Drawings

HYDROPHILIC, HIGHLY SWELLABLE HYDROGELS

The present invention relates to hydrophilic, highly swellable hydrogels which are coated with nonreactive, water-insoluble waxes.

BACKGROUND OF THE INVENTION

Hydrophilic hydrogels which can be obtained by polymerization of olefinically unsaturated acids, for example acrylic acid, methacrylic acid, acrylamidopropanesulphonic acid and the like, in the presence of small quantities of polyolefinically unsaturated compounds are already known and are described, for example, in U.S. Pat. Nos. 4,057,521, 4,062,817, 4,525,527, 4,286,082, 4,340,706 and U.S. Pat. No. 4,295,987.

Furthermore, disclosures have also been made of hydrophilic hydrogels which are accessible by graft copolymerization of olefinically unsaturated acids onto various matrices, for example polysaccharides, polyalkylene oxides and derivatives thereof (e.g. U.S. Pat. Nos. 5,011,892, 4,076,663, 4,931,497).

A characteristic of these hydrogels is their high absorption capacity for water and aqueous solutions, and they are therefore preferably used as absorbents in sanitary articles.

It is already known that the properties of these hydrogels can be modified by surface treatment with certain substances. For this purpose, conventional hydrogels, which are dried, ground and, if desired, sieved, are reacted in powder form with reactive compounds, i.e. with compounds which contain at least two groups which are able to form covalent bonds with the carboxyl groups of the hydrogels. The process is therefore one of crosslinking, which takes place on the surface of the gel particles.

Surface crosslinking of this kind is described, for example in EP-A-543303, where the surface-cross-linking agents employed are mixtures of phosphoric acid diglycidyl esters and other reactive compounds.

Numerous other processes describe the surface treatment and crosslinking of absorbent and swellable polymer particles with reactive compounds. For instance, U.S. Pat. No. 4,043,952 recommends improving the dispersibility in water by using polyvalent metal compounds, while U.S. Pat. No. 4,051,086 recommends improving the rate of absorption by using glyoxal. The documents EP-A-83022 (for improved dispersibility in water and to improve the absorption capacity), DE-A-3331644 (to improve the resistance to salt solutions, at a high water absorption rate), DE-A-3507775 (likewise to increase the salt resistance, at good liquid absorption and gel strength), DE-A-3523617 (to improve the flowability and to prevent caking), DE-A-3628482 (to improve the absorption of water on repeated use) and EP-A-349240 (to achieve an equilibrium between absorption capacity and rate of absorption and also gel strength and absorbency) describe the after treatment of polymers with crosslinking agents which contain bi- or polyfunctional groups, which agents are able to react with the carboxyl or carboxylate groups or other groups present in the polymer. In this case, the powder either mixed directly with the components, with or without the concomitant use of relatively small quantities of water and solvent, or the powder is dispersed in an inert solvent, or polymers containing from 10 to 40% by weight of water are dispersed in a hydrophilic or hydrophobic solvent and are subsequently or simultaneously mixed with the crosslinking agent. Crosslinking agents which can be used are polyglycidyl ethers, haloepoxy compounds, polyols, polyamines or polyisocyanates (see U.S. Pat. No. 4,666,983). In addition to these, DE-A-3314019, EP-A-317106 (in each case for achieving a high absorption quantity and high absorption rate) and DE-A-3737196 (high absorption capacity and high absorption rate coupled with great gel strength) additionally mention polyfunctional aziridine compounds, alkyl di- and tri-halides and oil-soluble polyepoxy compounds. In DE-A-3503458 (in order to achieve a polymer with good water absorption capacity, high water absorption rate and high gel strength with a non-tacky gel), a crosslinking agent is applied to a polymer resin in the presence of an inert inorganic powder material, such as $SiO_2$ without the use of organic solvents. Features common to all of these processes are that the resins are subsequently subjected to a temperature treatment and also that the crosslinking agents used for the surface treatment have at least two functional groups, i.e. are reactive. DE-A-4020480 describes a process for the surface crosslinking of hydrophilic absorbents by treatment with alkylene carbonates followed by thermal treatment at 150°–300° C. EP-A-509708 describes a process comprising the surface crosslinking of carboxyl-containing polymer particles with polyhydroxy compounds in combination with a surfactant coating.

A common feature of all of these polymer powders prepared by methods described above is that they comprise a certain amount of relatively fine particles which are responsible for so-called dusting and that in some cases these amounts of dust are significantly increased as a result of mechanical stress, for example by pneumatic conveying and the resulting abrasion. Fine dust, with a particle size of less than 10 µm, is undesirable for reasons of inhalation toxicity, while fine dust fractions less than 100 µm give rise to visible dusting, with all of its consequences, and lead to handling problems in production and processing operations, and these fractions are therefore likewise undesirable.

It should furthermore be stated that subsequent crosslinking of the surface of the gel particles does not achieve any reduction in the hygroscopicity of the dried polymer powders. This hygroscopicity leads to caking of the polymer powders in damp air and therefore causes considerable problems both in production and in processing operations.

It is known that the hygroscopicity of these polymer powders can be reduced by applying very fine inorganic, water-insoluble powders to the surface of the polymer particles. For instance, EP-A-388120 (reduction of hygroscopicity, cohesion and adhesion to metal surfaces) describes mixtures of a highly water-absorbent pulverulent polymer and a porous powder comprising a high-purity silica, the powder having an average particle size of from 0.1 to 30 µm and a specific surface area of 500 $m^2/g$ or more. The addition of such fine powders to the polymer powders, however, considerably intensifies the dust problem described above.

A further process for the surface treatment of hydrophilic hydrogels is aimed at improving the fixing of these hydrogels to fibre materials. For instance, EP-A-612533 describes the addition of hot-melt adhesives having adhesive properties at from 50° to 200° C. to hydrogels in order, for the use of these hydrogels in conjunction with fibre materials, to achieve the fixing of the hydrogel on the fibre material. Examples of the hot-melt adhesives used there are low molecular weight polyolefins, copolymers or paraffin wax. In order to achieve the desired fixing of the hydrogels to fibre materials, these hot-melt adhesives must be added in relatively large quantities. The addition of such relatively large quantities of hot-melt adhesive to the hydrogels, however, leads to a reduction in the absorption capacity of the hydrogels for aqueous liquids, which is undesirable.

SUMMARY OF THE INVENTION

The object of the present invention, therefore, is to provide dust-free abrasion-resistant highly swellable absorbents for aqueous liquids, having a low caking tendency in damp air. This object is, surprisingly, achieved by coating hydrophilic, highly swellable hydrogels which are known per se with only small quantities of non-reactive, water-insoluble waxes.

The present invention therefore relates to a hydrophilic, highly swellable hydrogel, characterized in that it is coated with a non-reactive, water-insoluble wax and the quantity of wax, based on the quantity of uncoated hydrogel, is from about 0.05% by weight to about 2% by weight. The wax may comprise a plurality of components.

The term "wax-coated hydrogel" should not be interpreted as meaning that the surface of the particles of the hydrogel powder is covered with a closed wax film. Rather, the surface of a hydrogel coated with the quantified of wax according to the invention has pores of sufficient size and sufficient number to have no adverse effect on the absorption properties of the hydrogel. If the hydrogel is coated with quantities of wax greater than those according to the invention, then the number and size of the pores decrease and there is an undesirable impairment of the absorption properties.

In this context, a wax is in particular to be understood—in accordance with the formulation of the German Society for Fat Science (DGF) of 1974 (see DGF standard methods: Analysis of fats, fat products and related substances, Section M: Waxes and wax products; Wissenschaf tliche Verlagsgesellschaf t, Stuttgart, 1975) as being a substance which is generally characterized, regardless of its chemical composition and its natural or synthetic origin, by the following physico-mechanical properties:

(1) kneadable at about 20° C., firm to hard-brittle;
(2) coarsely to finely crystalline, transparent to opaque, but not glass-like;
(3) melting above about 40° C. without decomposition;
(4) not thread-forming, and of relatively low viscosity, even only slightly above the melting point;
(5) highly temperature-dependent in consistency and solubility;
(6) polishable under slight pressure.

Particularly preferred waxes are those whose melting or dropping points are in the temperature range between about 30° and about 180° C., particularly preferably between about 40° and about 180° C. and, with very particular preference, between 40° and 170° C. The dropping point in this context is determined in accordance with the DGF standard method DGF-M-III 3 (75) (Wissenschaftliche Verlagsgesellschaft, Stuttgart).

Other particularly preferred waxes are those whose films have no tendency to become tacky in the temperature range between about 0° C. and about 80° C.

The waxes to be employed in accordance with the invention are non-reactive. This means, in the context of the present invention, that they have no reactive groups which are able to react with the carboxyl groups on the surface of the hydrogel particles.

The following list of Examples of waxes are not meant to be limiting, and exhaustive other waxes could work, but these are the preferred.

Examples of waxes to be employed in accordance with the invention are natural waxes, modified natural waxes, semisynthetic waxes and synthetic waxes. Examples of natural waxes are recent waxes, such as plant waxes or animal waxes. Examples of plant waxes are carnauba wax, candelilla wax, ouricuri wax, sugar-cane wax and retamo wax. Examples of animal waxes are insect waxes, such as beeswax, ghedda wax and schellac wax, and also wool wax. Further examples of natural waxes are fossil waxes, such as petroleum waxes or brown-coal (lignite) and peat waxes. Examples of petroleum waxes are ozokerite and tank-bottom wax, while an example of a brown-coal and peat wax is crude montan wax. Examples of modified natural waxes are the waxes obtained by refining, for example the macro- and microcrystalline paraffin waxes recovered from petroleum distillates or distillation residues, or chemically modified waxes, for example double-bleached crude montan wax. Examples of semisynthetic waxes are the acid waxes and ester waxes which can be prepared from montan wax, the wax acids which can be prepared by paraffin oxidation, and also alcohol waxes and amide waxes. Examples of synthetic waxes are hydrocarbon waxes, such as polyolefin waxes and FischerTropsch waxes, and synthetic waxes containing oxygen-functional groups. Examples of synthetic waxes containing oxygen-functional groups are acid waxes which are formed by oxidation of synthetic hydrocarbon waxes or by copolymerization or telomerization of olefins with unsaturated carboxylic acids, ester waxes which are obtained by esterifying synthetic wax acids with synthetic alcohols and by copolymerizing olefins with unsaturated esters, for example vinyl acetate, alcohol waxes which are prepared by oxo synthesis followed by hydrogenation and by hydrogenation of synthetic fatty acids, and amide waxes which are obtained by reacting synthetic acids with amines. Examples of waxes which are obtained by oxidation of synthetic hydrocarbon waxes are oxidation products (oxidates) of polyethylene waxes.

Preferred waxes for use in accordance with the invention are refined (i.e. deresinified and bleached) montan waxes and also polyolefin waxes.

Particularly preferred waxes for use in accordance with the invention are polyolefin waxes, such as polyethylene waxes (high-pressure polyethylene waxes, low-pressure polyethylene waxes, degradation polyethylene waxes), oxidates of these polyethylene waxes, waxes based on ethene-α-olefin copolymers, waxes based on ethenevinyl acetate copolymers, waxes based on ethene-styrene copolymers, waxes based on ethene-acrylic acid copolymers and waxes based on wax mixtures of polyethylene waxes with poly (tetrafluoroethylene) waxes.

It is also possible to employ mixtures of two or more of the above-mentioned waxes. In this case, the mixing ratios are not at all critical and should be adapted to the prevailing circumstances.

The hydrogel is preferably coated with wax in a quantity of from about 0.05 to about 1% by weight, particularly preferably in a quantity of from about 0.05 to about 0.95% by weight and, with very particular preference, in a quantity of from about 0.1% by weight to about 0.95% by weight, and preferably, furthermore, in a quantity of from about 0.2% by weight to about 0.8% by weight, based in each case on uncoated hydrogel.

The hydrophilic, highly swellable hydrogels on which the hydrogels according to the invention are based are, in particular, polymers comprising (co)polymerized hydrophilic monomers, graft (copolymers of one or more hydrophilic monomers on an appropriate graft base, crosslinked cellulose ethers or starch ethers, or natural products which are swellable in aqueous liquids, for example guar derivatives. These hydrogels are known and are described, for example, in the literature references cited above. Examples of suitable hydrophilic monomers are polymerizable acids, such as acrylic acid, methacrylic acid, vinylsulphonic acid, vinylphosphonic acid, maleic acid and its anhydridle, fumaric acid, itaconic acid, - 2-acrylamido-2-methylpropanesulphonic acid, 2-acrylamido-2-methylpropanephosphonic acid and amides thereof, hydroxyalkyl esters, and esters and amides containing amino groups or ammonium groups, and also water-soluble N-vinylamides or diallyidimethylammonium chloride.

Preferred hydrophilic monomers are compounds of the general formula I

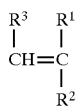
(I)

in which $R^1$ is hydrogen, methyl or ethyl, $R^2$ is the group —COR, the sulpho group, the phosphoric acid group, the phosphoric acid group which is esterified with $(C_1–C_4)$-alkanol, or is a group of the formula

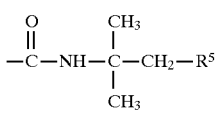

$R^3$ is hydrogen, methyl, ethyl or the carboxyl group, $R^4$ is hydroxyl, amino or hydroxy- $(C_1–C_4)$ -alkyl, and $R^5$ is the sulpho group, the phosphoric acid group, the phosphoric acid group which is esterified with $(C_1–C_4)$-alkanol, or is the carboxyl group.

Examples of $(C_1–C_4)$ -alkanols are methanol, ethanol, n-propanol, isopropanol or n-butanol.

Particularly preferred hydrophilic monomers are acrylic acid and methacrylic acid.

Suitable graft bases can be of natural or synthetic origin. Examples are starch, cellulose or cellulose derivatives, and other polysaccharides and oligo-saccharides, polyalkylene oxides, especially polyethylene oxides and hydrophobic polyesters. Suitable polyalkylene oxides have, for example, the formula

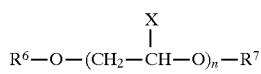

in which $R_6$ and $R^7$ independently of one another are hydrogen, alkyl, alkenyl or aryl, X is hydrogen or methyl, and n is an integer from 1 to 10,000.

$R^6$ and $R^7$ are preferably hydrogen, $(C_1–C_6)$-alkyl $(C_2–C_6)$-alkenyl or phenyl.

Examples of $(C_1–C_6)$ -alkyl are methyl, ethyl or n-butyl, while examples of $(C_2-C_6)$-alkenkyl are vinyl or allyl.

Preferred hydrogels are, in particular, polyacrylates, polymethacrylates, and the graft polymers described in U.S. Pat. Nos. 4,931,497, 5,011,892, 5,041,496. The content of these entire patents is expressly incorporated by reference in the present disclosure.

The hydrophilic, highly swellable hydrogels on which the hydrogels according to the invention are based are preferably crosslinked, i.e. they comprise compounds having at least two double bonds, which are incorporated by polymerization into the polymer network.

Particularly suitable crosslinking agents are methylenebisacrylamide and methylenebismethacrylamide, esters of unsaturated mono- or polycarboxylic acids with polyols, such as diacrylates or triacrylates, for example butanediol diacrylate or dimethacrylate, or ethylene glycol diacrylate or dimethacrylate, and trimethylolpropane triacrylate, and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid, and vinylphosphonic acid derivatives as described, for example, in EP-A-343427. The content of EP-A-343427 is also expressly incorporated by reference in the present disclosure.

Furthermore, the hydrophilic, highly swellable hydrogels on which the hydrogels according to the invention are based are with particular preference subsequently crosslinked in a manner known per se in the aqueous gel phase, or surface-crosslinked as ground and sieved polymer particles. Crosslinking agents suitable for this purpose are compounds containing at least two groups which are able to form covalent bonds with the carboxyl groups of the hydrophilic polymer. Examples of suitable compounds are di- or polyglycidyl compounds, such as phosphoric acid diglycidyl esters or glycidyl ethers of diols or polyols, alkoxysilyl compounds, polyaziridines, polyamines or polyamidoamines, it also being possible for the compounds mentioned to be used in mixtures with one another (see for example EP-A-83022, EP-A-543303 and EP-A-530438). Polyamidoamines which are suitable as crosslinking agents are described, in particular, in EP-A-349935. The content of the entire above-mentioned patent applications is also expressly incorporated by reference in the present disclosure.

The hydrophilic, highly swellable hydrogels on which the hydrogels according to the invention are based can be prepared by known polymerization methods. Polymerization is preferably carried out in aqueous solution according to the method of so-called gel polymerization. In this case, from about 15 to about 50% strength by weight aqueous solutions of one or more hydrophilic monomers and, if desired, of an appropriate graft base are polymerized in the presence of a free-radical initiator, preferably without chemical mixing, utilizing the TrommsdorffNorrish effect (Bios Final Rep. 363.22; Makromol. Chem. 1, 169 (1947)).

The polymerization reaction can be carried out in the temperature range between about 0° C. and about 130° C., preferably between about 10° C. and about 100° C., and either at atmospheric pressure or under elevated pressure. As is customary, the polymerization can also be performed under an inert-gas atmosphere, preferably under nitrogen.

The hydrogels according to the invention can be prepared by applying the non-reactive, water-insoluble waxes in the desired weight ratio to the powder, which is in general obtained by comminution, drying, grinding and sieving of the polymer, of the hydrophilic, highly swellable base hydrogels, and subjecting them to temperatures above the melting or dropping point of the waxes. This application operation is preferably carried out in mixers, for example twindrum mixers, so-called "ZIG-ZAG" mixers, horizontally operating ploughshare mixers, for example bridge mixers or cone-screw mixers, or perpendicularly cylindrical mixers with coaxially rotating blades, or else fluidizedbed mixers. The temperature treatment can be carried out at the same time as the application operation in a customary, above-described, heatable mixing apparatus. In a preferred embodiment, however, the temperature treatment step takes place in a downstream drier over a period of from about 5 minutes to about 6 hours. The temperature treatment takes place—depending on the melting or dropping point of the waxes to be employed—at from about 30° to about 200° C.

In this context, the non-reactive, water-insoluble waxes can be applied in powder form to the hydrophilic, highly swellable hydrogel powders.

Preferably, however, the non-reactive water insoluble waxes are employed in the form of an aqueous wax dispersion, wax emulsion or wax suspension. They can, however, also be employed in the form of a solution in an organic solvent or in a mixture of water and an organic water-miscible solvent. The aqueous dispersions, emulsions and suspensions mentioned may also include, as a component, an organic solvent which, if desired, is miscible with water.

Examples of suitable organic solvents are aliphatic and aromatic hydrocarbons, alcohols, ethers, esters and ketones, for example n-hexane, cyclohexane, toluene, xylene, methanol, ethanol, isopropanol, ethylene glycol, 1,2-propanediol, glycerol, diethyl ether, methyltriglycol, polyethylene glycols with an average molecular weight of about 200 to about 10,000, ethyl acetate, n-butyl acetate, acetone and 2-butanone.

Examples of suitable water-miscible organic solvents are aliphatic ($C_1$–$C_4$)-alcohols, for example methanol, isopropanol and tert-butanol, polyhydric alcohols, for example ethylene glycol, 1,2-propanediol and glycerol, ethers, for example methyltriglycol and polyethylene glycols having an average molecular weight of about 200 to about 10,000, and ketones, for example acetone and 2-butanone.

In the case of subsequently surface-crosslinked, hydrophilic, highly swellable hydrogels, the application is of the non-reactive, water-insoluble waxes can be carried out prior to, during or after the subsequent surface crosslinking step.

The present invention also relates to a process for reducing the dusting of a hydrophilic, highly swellable hydrogel, characterized in that the hydrogel is coated with a wax in a quantity of from about 0.05% by weight to about 2% by weight, based on the uncoated hydrogel. With regard to the hydrogel, the waxes, the application of the wax to the hydrogel and the preferred embodiment, the comments made above apply in a corresponding manner.

The hydrogels according to the invention are distinguished by outstanding mechanical stability, especially abrasion resistance. This is particularly the case on incorporation into sanitary articles. Furthermore, they exhibit only minimal formation of dust and show no tendency to cake in damp air.

They are therefore outstandingly suitable as absorbents for water and aqueous liquids, especially body fluids, for example urine or blood, for example in sanitary articles such as baby and adult nappies, sanitary towels, tampons and the like. However, they can also be used as soil conditioners in agriculture and horticulture, as moisture-binding agents in cable sheathing, and for thickening aqueous wastes.

The abrasion resistance and the anti-caking properties of the hydrogels according to the invention, which are described in the examples below, was determined.

The abrasion resistance was determined in a cylindrical porcelain mill having an internal diameter of 11 cm, an internal height of 11.5 cm, a capacity of about 1300 ml and associated metal balls (32 balls each having a diameter of about 0.9 cm and a weight of about 16.5 g, and one ball having a diameter of about 6.4 cm and a weight of about 1324 g) with an overall weight of about 1852 g. The vessel was charged with the balls and with 100 g of each of the polymer powders to be tested, and was then sealed and rolled for 30 minutes at 60 rpm on an appropriate roller drive. The polymer powder was subjected to a sieve analysis before and after this treatment, with the proportion in the lower particle-size range and the absorption under load (AUL) for different loads and different surface coverings being determined in particular.

The absorption under load was determined in a known manner as described, for example, in EP-A-339 461.

The anti-caking characteristics were determined by weighing 5.0 g of the polymer powder to be tested into a glass beaker and subjecting it to treatment for 30 minutes in a controlled-environment cabinet at a temperature of 40° C. and a relative atmospheric humidity of 95%. The anti-caking characteristics were then assessed visually, with an assessment scale ranging from 1 (free-flowing, powder free from lumps) to 5 (polymer powder completely caked together).

EXAMPLE 1

1 kg of super absorber prepared in analogy to Example 5 of DE-A4138408, whose content is expressly included in the present disclosure, was charged to a Telschig laboratory spray mixer RSM 6–60 with a capacity of 6 1. While mixing, a dispersion of 4 g of LANCO PE W 1555 and 30 g of water were sprayed onto these already surface-crosslinked super absorber granules over the course of 10 minutes with the aid of a dual-substance nozzle, and mixing was continued for 3 minutes. The product was subsequently dried at 140° C. in a drying oven for 30 minutes. Any lumps formed were removed by sieving through a sieve with a mesh size of 0.85 mm. The abrasion resistance and the anti-caking characteristics of the resulting product were determined as described above. The absorption under load was determined at a load of 40 g/cm$^2$ and a surface covering of 0.032 g/cm$^2$, using the particle-size fraction from 0.3 to 0.6 mm.

The experiment was repeated with three further wax grades. The results are shown in Table 1.

TABLE 1

| Wax grade | Anti-caking | before abrasion test | | after abrasion test | |
|---|---|---|---|---|---|
| | | AUL (g/g) | particle fraction <200 μm | AUL (g/g) | particle fraction <200 μm |
| no after-treatment | 4–5 | 23.0 | 10.5% | 15.9 | 27.9% |
| LANCO PE W 1555[a] | 1–2 | 29.2 | 10.0% | 27.3 | 16.0% |
| LANCO TF W 1765[b] | 1 | 29.1 | 8.3% | 26.2 | 16.5% |
| Hoechst wax DPE[c] | 2 | 27.5 | 9.8% | 24.3 | 18.8% |
| Hoechst wax PED 522[d] | 1–2 | 28.5 | 10.4% | 27.0 | 16.9% |

[a]LANCO PE W 1555 is a micronized polyethylene wax from Langer & Co.
[b]LANCO TF W 1765 is a polytetrafluoroethylene/polyethylene wax from Langer & Co.
[c]Hoechst wax DPE is an ester wax based on refined montan wax, from Hoechst AG.
[d]Hoechst wax PED 522 is a polar polyethylene wax from Hoechst AG.

EXAMPLE 2

1 kg of super absorber, prepared in analogy to Example 5a of DE-A-4138408, was charged to a Lödige laboratory mixer M5R. While mixing, 100 g of a crosslinking agent solution, consisting of 2.5% by weight of diglycidyl n-propylphosphonate, 2.5% by weight of monoethylene glycol diglycidyl ether (epoxy equivalent g/equ.=112), 47.5% by weight of isopropanol and 47.5% by weight of water, were sprayed onto these as yet not subsequently surface-crosslinked super absorber granules over the course of 5 minutes with the aid of a dual-substance nozzle and mixing was continued for 2 minutes. Subsequently, a dispersion of 4 g of Hoechst wax PED 522 and 30 g of water was sprayed onto these moist super absorber granules over the course of 5 minutes with the aid of a dual-substance nozzle, and mixing was continued for 2 minutes. The product was subsequently treated at 140° C. in a drying oven for 60 minutes. Any lumps formed were removed by sieving through a sieve having a mesh size of 0.85 mm.

The abrasion resistance and the anti-caking properties of the resulting product were determined as described above. Also determined was the dust fraction (particle <10 gm) by laser particle-size analysis by the dry dispersion method, following prior removal—by sieving—of the particles having a size of more than 250 gm, i.e. sieving through a sieve having a mesh size of 250 aim. This method of determination is suitable, however, only for relative measurements for comparison purposes, since because of the measurement method it gives excessively high values for the lower particle sizes.

The experiment was repeated with three further wax grades. In the control experiment, only the solution of crosslinking agent but not the wax dispersion was sprayed on. The results are shown in Table 2.

TABLE 2

| Wax grade | Anti-caking | Fine dust content[1] | Particle fraction <200 μm before abrasion test | Particle fraction <200 μm after abrasion test |
|---|---|---|---|---|
| Control experiment | 4–5 | 0.089% | 6.5% | 17.9% |
| Hoechst wax PED 522[d] | 1–2 | 0.032% | 5.8% | 10.1% |
| Hoechst wax DPE[c] | 2 | 0.042% | 5.2% | 9.8% |
| Hoechst wax S[e] | 2–3 | 0.047% | 6.2% | 10.7% |
| LANCO PE W 1555[a] | 1 | 0.024% | 4.9% | 8.1% |

[1]Content of fine dust having a particle size of less than 10 gm in the super absorber powder, given in percent is by weight
[a]LANCO PE W 1555 is a micronized polyethylene wax from Langer & Co.
[c]Hoechst wax DPE is an ester wax based on refined montan wax, from Hoechst AG.
[d]Hoechst wax PED 522 is a polar polyethylene wax from Hoechst AG.
[e]Hoechst wax S is an acid wax based on refined montan wax, from Hoechst AG.

EXAMPLE 3

1 kg of super absorber, prepared in analogy to Example 5a) of DE-A-4138408, and 4 g of LANCO PE W 1555 wax powder were intimately mixed over the course of 20 minutes in a Telschig laboratory spray mixer RSM 6–60 with a capacity of 6 1. This mixture was subsequently conditioned at 140° C. in an oven for 45 minutes. With renewed mixing in the Telschig laboratory spray mixer RSM 6–60, 100 g of a crosslinking agent solution, consisting of 2.5% by weight of diglycidyl n-propylphosphonate, 2.5% by weight of monoethylene glycol diglycidyl ether (epoxy equivalent g/equ.=112), 47.5% by weight of isopropanol and 47.5% by weight of water, were sprayed onto these super absorber granules over the course of 10 minutes with the aid of a dual-substance nozzle, and mixing was continued for 5 minutes. The product was subsequently treated at 140° C. in an oven for 60 minutes. Any lumps formed were removed by sieving through a sieve having a mesh size of 0.85 mm.

The abrasion resistance and the anti-caking characteristics of the resulting product were determined as described above.

The absorption under load was determined at a loading of 40 g/cm$^2$ and a surface covering of 0.032 g/cm2, using the particle-size fraction from 0.3 to 0.6 mm.

The experiment was repeated with two further wax grades. In the control experiment, the crosslinking agent solution was sprayed directly onto the super absorber prepared according to Example Sa) of DE-A-4138408, without mixing beforehand with wax powder. The results are shown in Table 3.

TABLE 3

| | | before abrasion test | | after abrasion test | |
|---|---|---|---|---|---|
| Wax grade | Anti-caking | AUL (g/g) | particle fraction <200 μm | AUL (g/g) | particle fraction <200 μm |
| control experiment | 4–5 | 24.5 | 6.8% | 18.5 | 18.5% |
| LANCO PE W 1555[a] | 1–2 | 29.7 | 5.7% | 26.8 | 8.4% |
| Hoechst wax PED 136[f] | 1–2 | 28.0 | 5.5% | 26.3 | 8.9% |
| Hoechst wax UL[g] | 2 | 26.9 | 6.2% | 25.8 | 10.3% |

[a]LANCO PE W 1555 is a micronized polyethylene wax from Langer & Co.
[f]Hoechst wax PED 136 is a polar polyethylene wax from Hoechst AG.
[g]Hoechst wax UL is an acid wax based on refined montan wax, from Hoechst AG.

We claim:
1. A hydrophilic, highly swellable hydrogel, comprising a cross-linked hydrogel coated with about 0.05 to about 2% by weight of a non-reactive, water insoluble wax, the quantity of the wax is based on the quantity of the uncoated cross-linked hydrogel.
2. The hydrogel according to claim 1, wherein the wax has a melting or dropping point in the temperature range between about 30° and about 180° C.
3. The hydrogel according to claim 1, wherein the wax is a refined montan wax.
4. The hydrogel according to claim 1, wherein the wax is a polyethylene wax or an oxidate of a polyethylene wax.
5. The hydrogel according to claim 1, wherein said hydrogel is coated with about 0.1 to about 0.95% by weight of the non-reactive, water in soluble wax, based on the quantity of the uncoated hydrogel.
6. The hydrogel according to claim 1, wherein the hydrogel is a polymer comprising (co)polymerized hydrophilic monomers, a graft copolymer of one or more hydrophilic monomers on a graft base, a crosslinked cellulose ether or starch ether, or a natural substance which is swellable in aqueous liquids.
7. A process for the preparation of a cross-linked hydrogel comprising applying a non-reactive, water-insoluble wax to a hydrophilic, highly swellable cross-linked base hydrogel.
8. A method of reducing the dusting of a hydrophilic, highly swellable cross-linked hydrogel, comprising coating a cross-linked hydrogel with a wax in a quantity of from about 0.05% by weight to about 2% by weight, based on the uncoated cross-linked hydrogel.
9. An absorbent for water and aqueous liquids comprising the cross-linked hydrogel as claimed in claim 1.
10. A process of absorption of body liquids comprising incorporating the cross-linked hydrogel as claimed in claim 1, into an absorbent material.
11. The hydrogel as claimed in claim 1, wherein said cross-linked hydrogel is solid.
12. The hydrogel as claimed in claim 1, wherein said cross-linked hydrogel is in a powdered form.
13. A process for the preparation of a cross-linked hydrogel comprising applying a non-reactive, water-insoluble wax to the hydrogel as claimed in claim 12.

14. A method of reducing the dusting of a hydrophilic, highly swellable cross-linked hydrogel, comprising coating the hydrogel as claimed in claim 12 with a wax in a quantity of from about 0.05% by weight to about 2% by weight, based on the uncoated hydrogel.

15. An absorbent for water and aqueous liquids comprising the hydrogel as claimed in claim 12.

16. A process of absorption of body liquids comprising incorporating the hydrogel as claimed in claim 12, into an absorbent material.

\* \* \* \* \*